United States Patent [19]

Korab

[11] Patent Number: 4,704,269

[45] Date of Patent: Nov. 3, 1987

[54] EFFERVESCENT ANTACID AND ANALGESIC COMPOSITIONS

[75] Inventor: Theodore J. Korab, Edison, N.J.

[73] Assignee: Hudson Pharmaceutical Corporation, West Caldwell, N.J.

[21] Appl. No.: 743,425

[22] Filed: Jun. 11, 1985

[51] Int. Cl.$^4$ .................. A61L 9/04; A61K 31/16; A61K 3/00

[52] U.S. Cl. .................. 424/44; 514/629; 514/819; 514/957; 514/960; 424/466

[58] Field of Search .................. 424/44, 14; 514/629, 514/819, 957, 960

[56] References Cited

U.S. PATENT DOCUMENTS

| | | | |
|---|---|---|---|
| 3,024,165 | 3/1962 | Murphy | 167/55 |
| 3,495,001 | 2/1970 | Leonards | 424/44 |
| 4,083,951 | 4/1978 | Goudie et al. | 424/44 |
| 4,093,710 | 6/1978 | Sass et al. | 424/44 |
| 4,309,408 | 1/1982 | Pathak et al. | 424/44 |

FOREIGN PATENT DOCUMENTS 769156  6/1971  Belgium .

OTHER PUBLICATIONS

Chem Abst., 98:1323382, 1983.

*Primary Examiner*—J. R. Brown
*Assistant Examiner*—John W. Rollins

[57] ABSTRACT

Disclosed are water soluble effervescent antacid, analgesic powder and tablet formulations which in a preferred embodiment are sodium, sucrose and aspirin free. The formulation is administered through the ingestion of an aqueous solution of the powder or tablet.

The powder and tablet formulations of this invention preferably comprise a therapeutically effective amount of acetaminophen as the analgesic and an effective amount of agglomerated particles of an antacid and a food grade acid which will react in an aqueous solution to produce visible gaseous effervescence.

The formulations of this invention preferably also comprise flavorants, which improve the taste and lubricants and hardening agents which aid in tableting the formulation.

32 Claims, No Drawings

EFFERVESCENT ANTACID AND ANALGESIC COMPOSITIONS

FIELD OF THE INVENTION

This invention disclosed herein relates to effervescent, aspirin-free analgesic and antacid powders and tablets made therefrom.

BACKGROUND OF THE DISCLOSURE

The prior art discloses pharmaceutical powder and tablet formulations which contain analgesic plus antacid ingredients. Tablet formulations of this type, such as Alka Seltzer also include components which produce effervescence when the tablet is placed in water. The effervescence aids in disintegrating or breaking-up the tablet when it is placed in water, and thereby assists in enhancing the rate at which the therapeutic components of the tablet dissolve in water. When the components of the tablet have completely dissolved in water the user then ingests the aqueous solution of the antacid and/or analgesic components.

A common analgesic employed in tablets and powders of the type described above is acetylsalicylic acid, commonly known as aspirin. However, it has become well known that, in sensitive individuals, aspirin leads to gastrointestinal upset and other undesirable side-effects. Moreover, the use of aspirin in children suffering from certain viral infections has been associated with the onset of Reyes Syndrome.

Due to the potential undesirable side effects which have been associated with the use of aspirin, acetaminophen, an aspirin substitute, has become the analgesic of choice. However, acetaminophen possesses a very pungent bitter flavor. The undesirable flavor and after-taste of acetaminophen is particularly prominent when acetaminophen is ingested in an aqueous solution due to the prolonged and extensive contact with the taste receptors (i.e., taste buds) of the tongue that occurs when a liquid is ingested.

In view of the foregoing, it is an object of this invention to provide a effervescent powder composition, and a tablet prepared therefrom, which is aspirin-free and is pleasant tasting.

In addition, effervescent tablet and powder formulations, such as those described above, typically employ various sodium salts as essential ingredients of the powder or tablet. For example, an antacid compound commonly employed in effervescent antacids is sodium bicarbonate. However, the ingestion of large amounts of dietary sodium has been associated with the onset or exacerbation of hypertension in some sensitive individuals. Moreover, food stuffs containing sodium are often intentionally excluded from the diet of individuals suffering from hypertension and a variety of other diseases.

Furthermore, conventional antacid/analgesic tablet and powder formulations often contain sucrose (table sugar) as a sweetening agent. The pharmaceutically active ingredients typically employed in the foregoing formulations sometimes have an undesirable and unpalatable flavor and sucrose sugar is typically added to counter-act or mask this unpleasant taste. Sucrose, however, is known to cause tooth decay and also should be avoided by certain individuals for medical reasons (i.e., diabetics).

It is, therefore, a further object of this invention to provide a palatable and pleasant testing effervescent antacid, analgesic powder and tablet formulation which is both sodium-free and sucrose free.

Finally, shelf-stability is an important property of any commercially available effervescent tablet formulation. This is because tablets, after being formulated and packaged, may be stored for considerable lengths of time before being purchased and used by a consumer.

It is, therefore, yet another object of the invention to provide a shelf-stable effervescent antacid, analgesic tablet formuation. The tablets of this invention are shelf-stable for at least about 6 to about 24 months or more when packaged in conventional air-tight packaging.

SUMMARY OF THE INVENTION

In summary, the invention disclosed herein comprises an antacid and analegesic powder formulation suitable for the preparation of a shelf-stable tablet which is aspirin-free and, which preferably is both sucrose and sodium-free, but which produces visible carbon dioxide effervescence when placed in water.

In preferred embodiments the powder and tablet compositions of this invention comprise a therapeutically effective amount of acetaminophen and a therepuetically effective amount of fused granules (e.g. agglomerated particles) of an antacid salt and a food grade acid which in an aqueous solution reacts with the antacid component to produce gaseous effervescence. The agglomerate particles are present in the powder and tablet formulations of this invention in an amount at least sufficient to produce a visible amount of effervescence when the composition is placed in from about 100 about 1000 cc of water.

The powder and tablet formulation of this invention also includes flavorants, as well as minor but effective amounts of other ingredients which assist in the formation of shelf-stable tablets which do not disintegrate or break apart over prolonged shelf-storage, and which do not effervesce prematurely when packaged in conventional moisture-proof packaging. The ingredients which assist in the tableting of the powder composition of this invention include lubricants and tablet hardening agents.

DETAILED DESCRIPTION OF THE INVENTION

The pharmaceutical compositions of the present invention are comprised of an effective amount of a non-aspirin analgesic compound, as well as a therapeutically effective amount of an antacid component. The non-aspirin analgesic is preferrably acetaminophen, although other non-aspirin analgesics, which are not associated with gastrointestinal upset may be employed in place of or in combination with acetaminophen.

As described in greater detail below, the antacid component is preferably employed in the form of an agglomerate of fine individual particles of an antacid compound and fine particles of a solid food grade acid capable of reacting with the antacid compound in aqueous solution to produce carbon dioxide effervescence. The preferred antacid compound for use in the agglomerate are the salts of $HCO_3$ or $CO_3$, (i.e. bicarbonate or carbonate) and most preferably potassium bicarbonate in the sodium-free formulations of this invention. Although, if a sodium containing formulations is desired, antacid sodium salts may be used. The preferred acid for use in tne agglomerate is citric acid.

The powder and tablet formulation of the present invention preferably comprise about 45% to about 75% by weight of the agglomerate component, and most preferably about 55% to about 70% by weight of the antacid containing agglomerate. The non-aspirin analgesic component preferably comprises about 5% to about 12% by weight of the formulation, and most preferably about 6% to about 8%.

The agglomerate component of the powder and tablet formulation is preferably prepared by agglomerating together finely divided solid particles of a bicarbonate or carbonate salt having antacid properties, and a solid food grade acid. The agglomerate may be prepared by applying an edible, nontoxic and water soluble binding agent to an agitated fluidized bed of finely ground antacid and acid particles.

The agglomerates present in the powder or tablet provide therapeutic amounts of the antacid when the composition is ingested. In addition, when placed in water the acid component and antacid component chemically react to provide a visible amount of effervescence when the powder or the tablet is placed in the volume of water held by an ordinary drinking glass. Preferably, the agglomerate content of the tablet and powder formulations of this invention is such that visible amount of effervescence is produced when the tablet is placed in from about 100 to about 1000 cc of water.

The above-described agglomerating process advantageously binds the acid in close proximity to the antacid component. Since it is the reaction between the acid and the antacid component which produces effervescence in water, the close proximity of the acid and antacid within the agglomerate is believed to enhance the onset and rate of effervescence when the tablet or powder of this invention is placed in water.

The agglomerate employed herein may be prepared by any one of a number of techniques known to the art for forming stable particulate agglomerate from finely divided powder particles. For example, the agglomerate employed herein may be formed by placing the antacid and the acid both of which are comprised of fine powder particles into a fluid bed granulator. A fluid bed granulator such as a Glatt Powder Coater may be employed for this purpose. In a Glatt Powder Coater a jet of air is employed to fluidize a bed of powder particles, i.e. to puff-up the particles and suspend them in air. A spray of a food compatable and water soluble food grade binder is then applied to the fluidized particles and at the same time fluidized bed is agitated in a rotary manner. As the binder is applied to the fluidized particles they agglomerate in a snow ball-like manner into larger and larger agglomerates as the amount of binder applied increases.

An advantage associated with the use of a fluid bed granulator is that very little of the liquid carrier which contains the binding agent is retained by the agglomerated product. The preferred liquid carrier for the binding agent is water. If too much water is present in the agglomerates, the agglomerates may effervesce prematurely, i.e., during the powder or tablet forming process or while the powder or tablets are being stored. The agglomerate should be substantially anhydrous and should posses a moisture content of less than about 0.1 to about 0.15% moisture.

Moreover, agglomeration in a fluid bed granulator is typically conducted at room temperature and, hence, avoids subjecting the components of the agglomerate to elevated temperatures which might adversely affect the antacid or acid ingredients.

The agglomerate preferably comprises between about 40% and about 60%, and most preferably about 50% to about 55% of the carbonate, or bicarbonate or mixtures thereof (i.e. the antacid component) with potassium bicarbonate being the preferred. The antacid has a preferred particle size of 30 to 100 mesh with the most preferred particle size being between about 40 to about 60 mesh.

The acid component of the agglomerate may comprise any food grade acid preferrable a hydoxylated organic carboxylic acid or salt thereof. The agglomerate preferably comprises from about 35% to about 55% and most preferably about 40% to about 45% by weight of the acid. Suitable acids include citric, tartaric, fumaric, malic and other like acids, with citric acid being preferred. The acid has a preferred particle size of about 30 to about 100 mesh with the most preferred particle size being between about 40 to about 60 mesh.

The binder used in the invention may be any water soluble food grade binder. The binder is present in the agglomerate in sufficient quantities to bind together the acid and antacid components. For example, in an agglomerate comprised of about 50% to about 55% antacid and about 40% to about 45% acid, the binder preferably comprises from about 3% to about 8% of the agglomerate.

The preferred binder for use in the invention is a maltodextrin, which is a powder, however, other food grade materials capable of adhering together the antacid and acid particles of the agglomerate may by employed. A commercially available maltodextrin found to be suitable for use in the present invention is M-100 Maltrin available from Grain Proccessing Co. of Iowa.

Water is the liquid carrier most preferred for carrying the binder which is applied during the agglomeration process. This is because most of the food grade binders are soluble in water and water is is relatively easy to flash off the agglomerated particles. The binder/carrier solution is prepared by dissolving a sufficient amount of binder into the liquid carrier to provide for the preferred binder concentration in the final agglomerated particles.

As was described above, water content of the agglomerate particles is important in the context of the present invention. The agglomerate product is preferably substantially anhydrous, however, a low-moisture content of preferably less than about 0.1% to about 0.15% may be present in the agglomerate without unduly limiting the shelf-life of the product.

Moreover, in order to provide a tablet wherein the component granules are firmly bound together, and do not prematurely disintegrate upon standing, it is prefered to employ agglomerates having a particle size such that 100% of the granules will pass through about a 10 mesh screen, with no more than about 5% of the agglomerate granules passing through about a 40 mesh screen.

Because of the extreme bitter taste of the acetaminophen, the powders and tablets of the present invention preferably further comprise from about 1% to about 8% and most preferably about 3% to about 5% by weight of a flavorant ingredient or composition which masks the undesirable flavor of the acetaminophen and enhances the overall palatability of the formulation. The flavorant may be comprised of admixtures of several different classes of flavorants. These classes include spray dried flavors, nonsugar sweeteners (sugar sweeteners may be used but are not prefered) and food grade acids. The amounts and classes of flavorants employed in a given formulation may be selected on the basis of the particular flavor desired for the tablet or powder formulation within the scope of this invention.

A wide variety of spray dried flavors which may be employed herein are known to the art. Spray dried flavors are the solid powdered flavor essences distilled from liquid extracts of fruit or other natural products. In order to enhance the palatability of the acetaminophen composition of this invention, a combination of grapefruit and bitter almond flavors is preferred.

A wide variety of food grade acids may also be included in the formulation of the present invention. Such acids function to enhance the taste or flavor masking effect of the spray dried flavors or other flavorant ingredients present in the formulation. Examples of the food grade acids suitable for use herein include acids such as tartaric, malic, citric and fumaric acids or any other suitable non-toxic acid of this type.

In the preferred embodiments of the present invention, the analgesic and antacid composition is sugar (sucrose) free. In such sucrose-free formulations, in order to reduce the undesirable flavor impact of acetaminophen and/or to provide tne aqueous solution of the tablet or powder compositions of the present invention with a sweet taste, a wide variety of non-sucrose sweeteners may be employed. For example, the formulations of the invention may include minor flavoring amounts of fructose which is a sugar of low caloric value, or a mixture of the known sugar-substitute sweeteners, such as calcium saccharin, glycine, aspartame, sorbitol and the like.

The preferred combination of flavorant ingredients employed in the formulations of this invention comprises from about 0.25% to about 1.5% grapefruit spray dried flavor, from about 0.1% to about 0.2% bitter almond spray dried flavor, from about 1% to about 2% tartaric acid and from about 0.3% to about 0.8% calcium saccharin. This combination sufficiently masks the extreme bitter taste of the acetaminophen and, therefore, provides for palatable powder or tablet formulations.

If the composition of the present invention is to be made in tablet form, the formulation may include any one or more of the conventional ingredients known in the art to assist the tableting of powders. For example, a powder intended for tableting may include from about 1.0% to about 4.0% of a lubricant. The presence of the lubricant aids in the tablet-making process as described in detail below. Typical of the lubricants useful in the present invention are glycine, talc, magnesium, calcium and zinc stearate, polyethylene glycol, lubritab, or other hydrogenated vegetable or unsaturated oils and the like. The lubricants prevent the powder from sticking to the tablet forming punches and dies or molds when pressure is applied during a compresive tableting process. In addition, the lubricant allows the powder particles to "slide" past each other to a certain extent so they can be packed tightly together in the tablet form.

In addition to the lubricant, the compositions of the invention adapted for tableting preferrably also contain about 15% to about 25% by weight of a tablet hardening agent. Suitable hardening agents include sorbitol, sucrose, dextrose, lactose and the like. The function of this agent is to provide for tablet cohesiveness. The preferred tablet hardening agent for use herein is sorbitol. Sorbitol has the property that it binds together particles which do not normally bind well together. When used in the present invention, a tablet is produced that good hardness and which is shelf-stable for on the average of 6 to 24 months or more.

The composition of the present invention may be prepared by thoroughly blending together the acetaminophen with a portion of the lubricant and a portion of the flavorants to form a preblend. The preblend is screened through a 20 mesh screen eliminate over-sized particles from the mix.

The screened preblend is then placed in a blender and is thoroughly blended with the agglomerate particles, additional flavorant, lubricant and the tablet hardening agent (e.g. Sorbitol). Of course, the lubricant and the hardening agent are employed only if the formulation is to be formed into tablets.

The tablets are formed by placing a portion of the powder mixture containing the lubricant and hardening agent described above in a tablet press, and compressing the mixture at high pressure. Following their formation, the tablets are stabilized by heating the tablets to approximately 160° F. for about one hour. The stabilization step is used to drive off any residual water left over in the tablets from the agglomeration process and thereby avoids pre-mature effervesce during storage of the product. The stabilization step is preferrably performed even if the formulation of the present invention is to be used in powder form.

The formulation of the present invention is used by mixing an effective amount of the formulation with water to form an effervescent solution. The effervescence aids in breaking up the tablets and dissolving the formulation into the water. When effervescence is complete the solution of the tablet or powder in water will typically be complete and the solution may then be ingested. The effective dosage of the composition to be dissolved in water of the present invention may range from preferably about 3 to 10 grams in about 150–400 cc of water. If used in tablet forms the effective dosage is preferably delivered in one to two tablets.

It will be obvious to those skilled in the art that the powder and tablet formulations of the present may further comprise conventional excipients typically included in orally adminsterable composition. These materials include fillers, colorants, food dyes and the like.

The invention is further illustrated by the following examples:

EXAMPLE I

An effervescent antacid and analgesic compositon may be prepared by mixing the following components in the amounts indicated:

| Components | Amount (g) |
|---|---|
| Acetaminophen | 7.2 |
| glycine | .9 |
| calcium saccharin | .7 |

The above components are blended together for approximately five minutes and then screened through a 20 mesh screen to form a preblend.

In a fluid bed granulator, 53 grams of potassium bicarbonate and 42 grams of citric acid are placed. The mixture is suspended in the granulator and sprayed with a maltodextrin/water solution. The suspended particles form agglomerated granules having a particle size such that 100% of the granules pass through a 10 mesh screen with less than 5% of the granules passing through a 40 mesh screen. The resulting agglomerated granules should contain about 5 grams of the maltodextrin and have a moisture content of less than 0.15%.

All of the preblend along with 66 grams of the agglomerate is placed in a blender. In addition, 1.5 grams of tartaric acid, 1.2 grams of sprayed dried grapefruit flavor, 0.3 grams of talc, 0.15 grams of sprayed dried bitter almond flavor and 22 grams of sorbitol are added to the blender. The mixture is blended for five minutes. To the blender is then added 0.04 grams of magnesium stearate which has been screened through a 30 mesh screen. The mixture is then blended for an additional one (1) minute. The resulting powder is aspirin, sucrose and sodium-free mixture.

EXAMPLE II

The powder mixture formulated in accordance with example I may be compressed into a tablet having a 1.0 inch diameter and a thickness of 0.255 inches. The resulting tablets will weigh approximately 4.5 gram each and will have a hardness of 5-10 kg as measured on a Pfizer Hardness Tester.

What is claimed is:

1. A water soluble antacid and analgesic powder which effervesces in water comprising a therapeutically effective amount of a non-aspirin analgesic compound in admixture with a therapeutically effective amount of a substantially anhydrous agglomerate comprised of particles of an antacid and particles of a food grade acid reactive with said antacid in aqueous solution to produce carbon dioxide effervescence, wherein said particles of antacid and particles of acid are bound together by a water soluble food grade binder to form said agglomerate.

2. The powder according to claim 1 wherein said antacid is selected from the group consisting of a sodium-free salt of a bicarbonate or carbonate and mixtures thereof.

3. The powder of claim 2 wherein the antacid is potassium bicarbonate.

4. The powder of claim 3 wherein said antacid comprises from about 40% to about 60% of the agglomerate.

5. The powder of claim 2 wherein the acid is selected from the group consisting of citric, malic, tartaric and fumaric acid.

6. The powder of claim 5 wherein the acid comprises from about 35% to about 55% by weight of the agglomerate.

7. The powder of claim 6 wherein the acid is citric acid and said antacid is potassium bicarbonate.

8. The powder of claim 1 wherein said antacid agglomerate comprises from about 45% to about 75% by weight of the powder composition.

9. The powder of claim 1 wherein the effective amount of said analgesic is from about 5% to about 12% by weight of the powder composition.

10. The powder of claim 1 wherein the non-aspirin analgesic is acetaminophen.

11. The powder of claim 10 further comprising from about 1% to about 8% of a flavorant sufficient to enhance the palatability of aqueous solutions of said powder.

12. The powder of claim 11 wherein said flavorant is selected from the group consisting of a spray dried flavor, a non-sucrose containing a sweetener, a food-grade acid and mixtures thereof, wherein said powder is free of sucrose and sodium-containing ingredients.

13. The powder of claim 12 wherein the spray dried flavor is selected from the group consisting of grapefruit flavor, bitter almond flavor and mixtures thereof; wherein the non-sugar sweetener is selected from the group consisting of fructose, glycine, sorbitol, calcium saccharin, aspartame or mixtures thereof; and wherein said acid is selected from the group consisting of malic, fumaric, tartaric, and citric acid and mixtures thereof.

14. A water soluble effervescent antacid and analgesic powder comprising:
from about 55% to about 70% by weight of an antacid agglomerate, wherein said agglomerate is comprised of particles of potassium bicarbonate and citric acid agglomerated together with a maltodextrin binding agent;
from about 6% to about 8% of acetaminophen; and
from about 2% to about 8% of a flavorant selected from the group consisting of spray dried flavoring, a non-sugar sweetener, a food-grade acid and mixtures thereof, and wherein said powder is aspirin, sucrose and sodium free.

15. A water soluble antacid and analgesic tablet which effervesces in water comprising a therapeutically effective amount of a non-aspirin analgesic compound in admixture with a therapeutically effective amount of an agglomerate comprised of particles of an antacid and particles of a solid food grade acid reactive with said antacid to produce carbon dioxide effervescence, wherein said particles of acid and said particles of antacid are bound together by a water soluble food grade binder to form said agglomerate.

16. The tablet according to claim 15 wherein said antacid is selected from the group consisting of a sodium-free salt of a bicarbonate or a carbonate and mixtures thereof.

17. The tablet of claim 16 wherein the antacid comprises from about 40% to about 60% of the agglomerate and wherein said acid comprises from about 35% to about 55% of the agglomerate.

18. The tablet of claim 17 wherein the antacid is potassium bicarbonate.

19. The tablet of claim 17 wherein the acid is selected from the group consisting of citric, malic, tartaric and fumaric acid.

20. The tablet of claim 15 wherein said antacid agglomerate comprises from about 45% to about 75% by weight of the tablet composition.

21. The tablet of claim 15 wherein the effective amount of said analgesic is from about 5% to about 12% by weight of said tablet composition.

22. The tablet of claim 21 wherin said non-aspirin analgesic is acetaminophen.

23. The tablet of claim 15 further comprising from about 1% to about 4% by weight of a lubricant and from about 15% to about 25% by weight of a hardening agent.

24. The tablet of claim 23 wherein the lubricant is selected from the group consisting of glycerine, talc, magnesium stearate, calcium stearate, zinc stearate polyethylene glycol, hydrogenated vegetable oils, unsaturated oils and mixtures thereof, and the hardening agent is selected from the group consisting of sorbitol, lactose, and fructose.

25. The tablet of claim 24 further comprising from about 1% to about 8% by weight of flavorant.

26. The tablet of claim 25 wherein the agglomerate particle size is such that the 100% of the agglomerate passes through a 10 mesh screen while no more than 5% of the agglomerate passes through a 40 mesh screen.

27. The tablet of claim 25 wherein the flavorant is selected from the group consisting of a spray dried flavor, a non-sucrose containing sweetener, a food-grade acid and mixtures thereof, wherein said tablet is free of sucrose and sodium containing ingredients.

28. The tablet of claim 27 wherein the spray dried flavor is selected from the group consisting of grape fruit flavor, bitter almond flavor and mixtures thereof; wherein the non-sugar sweetener is selected from the group consisting of glycine, calcium sacharin, aspartame and mixtures thereof; and wherein said food grade acid is selected from the group consisting of tartaric, malic, fumaric and citric acid and mixtures thereof.

29. An effervescent antacid, analgesic tablet comprising:
from about 55% to about 70% of an antacid agglomerate comprised of particles of potassium bicarbonate and citric acid agglomerated together with a maltodextrin binder;
from about 6% to about 8% of acetaminophen;
from about 1% to about 8% of a flavorant selected from the group consisting of a spray dried flavor, a non-sugar sweetener, hydroxy carboxylic acid and mixtures thereof;
from about 2% to about 4% of a lubricant; and
from about 15% to about 25% of a tablet hardening agent.

30. A method for treating a mammal suffering from gastro-intestinal distress, the method comprising orally administering to the mammal a solution comprised of an effective amount of the powder of claim 14 dissolved in water.

31. A method for treating a mammal suffering from gastro-intestinal distress, the method comprising orally administering to the mammal a solution comprised of an effective amount of the tablet of claim 29 dissolved in water.

32. The method of claim 30 or 31 wherein said effective amount is from about 3 gms to about 10 gm in about 150 to 400 cc of water.

* * * * *